United States Patent [19]

Tam

[11] Patent Number: 6,069,267

[45] Date of Patent: *May 30, 2000

[54] SELECTIVE SYNTHESIS OF ORGANODIPHOSPHITE COMPOUNDS

[75] Inventor: Wilson Tam, Boothwyn, Pa.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/113,260

[22] Filed: Jul. 10, 1998

Related U.S. Application Data

[60] Provisional application No. 60/054,002, Jul. 29, 1997.

[51] Int. Cl.$^7$ ....................................................... C07F 9/145
[52] U.S. Cl. .................................. 558/95; 558/92; 558/96; 558/156
[58] Field of Search .................................. 558/92, 95, 96, 558/156

[56] References Cited

U.S. PATENT DOCUMENTS

| | | | |
|---|---|---|---|
| 3,245,979 | 4/1966 | Nelson . | |
| 3,484,506 | 12/1969 | Baranauckas . | |
| 3,488,407 | 1/1970 | Schall et al. | 260/927 |
| 4,668,651 | 5/1987 | Billig et al. | 502/158 |
| 4,769,498 | 9/1988 | Billig . | |
| 5,235,113 | 8/1993 | Sato et al. | 568/454 |
| 5,254,741 | 10/1993 | Lorz et al. | 568/454 |
| 5,312,996 | 5/1994 | Packett . | |
| 5,391,801 | 2/1995 | Sato . | |
| 5,401,845 | 3/1995 | Pitteloud . | |
| 5,663,369 | 9/1997 | Kreutzer . | |
| 5,696,280 | 12/1997 | Shapiro | 558/140 |
| 5,821,378 | 10/1998 | Foo et al. | 558/338 |

FOREIGN PATENT DOCUMENTS

| | | |
|---|---|---|
| 0 472 071 B1 | 6/1993 | European Pat. Off. . |
| 0 577 042 A1 | 1/1994 | European Pat. Off. . |
| WO 96/22968 | 8/1996 | WIPO . |

OTHER PUBLICATIONS

Tetrahedron Asymmetry by Sakai vol. 3 No. 5 pp. 583–586 1992.

Advances in Inorganic Chemistry by Cotton and Wilkenson p. 375 1972.

*Primary Examiner*—Gary Geist
*Assistant Examiner*—Jean F Vollano

[57] ABSTRACT

A process for the preparation of organodiphosphites of the formula $(R^1O)_2P(OZO)P(OR^1)_2$ wherein $R^1$ and Z are different substituted or unsubstituted aryl groups.

10 Claims, No Drawings

SELECTIVE SYNTHESIS OF ORGANODIPHOSPHITE COMPOUNDS

RELATED APPLICATION

This application claims the benefit of U.S. provisional application Ser. No. 60/054,002, filed Jul. 29, 1997.

FIELD OF THE INVENTION

This invention relates to a process for the synthesis of organodiphosphites.

BACKGROUND OF THE INVENTION

Organodiphosphites are known to be useful as ligands for metal-complex catalysts which are useful in hydrocyanation reactions. Particularly useful organodiphosphites are those of the general structure:

$(RO)_2P(OZO)P(OR)_2$.

The synthesis of these organodiphosphites can be accomplished by reacting a mixture of at least one alcohol (ROH) and a diol (HOZOH) with phosphorous trichloride under conditions which allow resulting HCl to be distilled away, often at elevated temperature. This kind of synthesis can result in the production of a reaction product which also contains unwanted byproducts. These byproducts can include various organomonophosphites. These byproducts can also include unwanted organodiphosphites, including those of the formulae shown below:

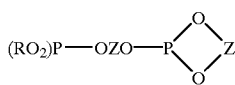

and

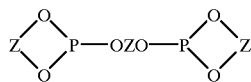

Depending upon the relative amounts of ROH and HOZOH in the alcohol/diol mixture, the reaction product of the alcohol/diol mixture and $PCl_3$ may contain the desired organodiphosphite in unacceptably low yields.

In general, laboratory approaches to selectively producing organodiphosphites involve carrying out the reaction in the presence of a base such as trialkylamine under extreme cold conditions (e.g. −78° C.). Although desired organodiphosphites can be produced, they can undergo molecular rearrangement in the presence of acid to yield unwanted byproducts. A combination of carrying out the reaction in the presence of a base and in extreme cold can effectively slow down rearrangement to allow for a selective synthesis of the desired organodiphosphites through sequential addition of the alcohols and diol.

However, extreme cold is impractical from a commercial viewpoint, and there have been attempts to carry out selective synthesis under more practical conditions. In WO96/22968, a multistep process for the synthesis of compounds of the type $(ArO)_2P(O-Z-O)P(OAr)_2$ where Ar and Z are substituted or unsubstituted aryl groups is described in which all steps are carried out at 0° C. or above with selectivity of about 90% reported. The process involves the synthesis of intermediate phosphoramidite compounds $(RO)_2P-N(R')_2$, which are then converted to phosphorchloridites, $(RO)_2PCl$, by reacting the phosphoramidites with anhydrous HCl, and then reacting the phosphorchloridites with base and the organic diol, HO—Z—OH, to produce the desired organodiphosphite.

U.S. Pat. No. 5,235,113 discloses a room temperature process for the preparation of a phosphite having a formula $(RO)_2P(O-A-O)P(OR)_2$ where A is biphenyl and R is 3,6-di-t-butyl-2-napthyl. The process involves reacting a solution of 4 molar equivalents of 3,6-di-t-butyl-2-naphthol (an ROH material) and 4 molar equivalents of triethylamine (a base) with 2 molar equivalents of $PCl_3$ by dropwise addition to produce a phosphorchloridite intermediate. This product is then reacted with one molar equivalent of 2,2'-biphenyldiol (an HOZOH) and 2 molar equivalents of triethylamine by dropwise addition.

U.S. Pat. No. 4,668,651 discloses a process for making certain symmetric organodiphosphites by reacting an organic diphenolic compound with phosphorous trichloride to form a phosphorochloridite intermediate and then reacting the intermediate with a diol.

The process of WO96/22968 produces acceptable products, but it is a relative high cost multistep process. The process of U.S. Pat. No. 5,235,113 is simple, but can result in low yields of certain organodiphosphites, depending on the nature of the ROH reactant.

It would be desirable to have a process for producing organodiphosphites in high yield, good selectivity and at a commercially desirable cost. These objectives are met by the process of the present invention.

SUMMARY OF THE INVENTION

The present invention provides a process for the preparation of organodiphosphites of the general formula $(R^1O)_2P(OZO)P(OR^1)_2$ wherein $R^1$ and Z are different substituted or unsubstituted aryl groups, which comprises:

(a) treating at a temperature between about −25° C. and 10° C. one molar equivalent of $PCl_3$ with about two molar equivalents of $R^1OH$;

(b) treating the solution of step (a) at between about −25° C. and 10° C. with at least two equivalents of an organic base to produce $(R^1O)_2PCl$ and a substantially insoluble salt formed from the organic base and HCl which is formed by the reaction of $R^1OH$ and $PCl_3$; and (c) reacting at a temperature of between about −25° C. and 10° C. the $(R^1O)_2PCl$ with about one half molar equivalent of HO—Z—OH, provided if less than three equivalents of the organic base are utilized in step (b), then a sufficient quantity of additional organic base is added to bring the total equivalents of organic base utilized in the process to at least three.

DETAILED DESCRIPTION

The present invention provides a simple process for the selective synthesis of organodiphosphites of the formula, $(R^1O)_2P(OZO)P(OR^1)_2$, wherein $R^1$ and Z are different substituted or unsubstituted aryl groups. The term "aryl group" denotes an organic radical which is derived from an aromatic hydrocarbon. The process involves sequentially treating $PCl_3$ with about two molar equivalents of $R^1OH$, adding an organic base, and then adding HO—Z—OH. This reaction results in the generation of HCl. A critical feature of the process is that all reactions are carried out below 10° C. and in a solvent in which the organodiphosphite product is soluble, but the byproduct salt formed by the reaction of the organic base and HCl is insoluble. The addition of base is necessary to drive the reaction between $PCl_3$ and $R^1OH$ to completion. The byproduct salt of the organic base is then removed from the product mixture by aqueous extraction. The organic solvent may be flash distilled to isolate a product mixture which typically contains the desired product with about 70% to 90% selectivity. Other phosphite byproducts such as $P(OR^1)_3$, or $R^1OP(O-Z-O)$ make up the balance of the product mixture. The purity of the crude reaction product is often acceptable for further use. However, if greater purity is desired, the mixture may be subjected to standard purification methods such as fractional distillation or crystallization methods, as appropriate.

The preferred product of the present process is an organodiphosphite of the formula $(R^1O)_2P(OZO)P(OR^1)_2$, wherein $R^1$ is phenyl, unsubstituted or substituted with is one or more $C_1$ to $C_{12}$ alkyl or $C_1$ to $C_{12}$ alkoxy groups; naphthyl, unsubstituted or substituted with one or more more $C_1$ to $C_{12}$ alkyl or $C_1$ to $C_{12}$ alkoxy groups; anthracenyl, unsubstituted or substituted with one or more $C_1$ to $C_{12}$ alkyl or $C_1$ to $C_{12}$ alkoxy groups; or phenanthrenyl, unsubstituted or substituted with one or more $C_1$ to $C_{12}$ alkyl or $C_1$ to $C_{12}$ alkoxy groups. Particularly preferred $R^1$ groups are 2-methylphenyl (2-tolyl), 2-methoxyphenyl, 3,5-di-tert-butylphenyl, 1-naphthyl, 9-phenanthrenyl, 2-isopropylphenyl, 2-isopropyl-5-methylphenyl, and 2-ethylphenyl.

Preferably, Z is selected from radicals defined by the formulae I to IV:

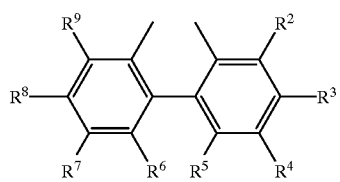

I where:
- $R^2$ and $R^9$ are the same and are selected from H, $C_1$ to $C_{12}$ alkyl, and $C_1$ to $C_{12}$ alkoxy;
- $R^3$ and $R^8$ are the same and are selected from H, $C_1$ to $C_{12}$ alkyl, and $C_1$ to $C_{12}$ alkoxy;
- $R^4$ and $R^7$ are the same and are selected from H, $C_1$ to $C_{12}$ alkyl, and $C_1$ to $C_{12}$ alkoxy;
- $R^5$ and $R^6$ are the same and are selected from H, $C_1$ to $C_{12}$ alkyl, and $C_1$ to $C_{12}$ alkoxy; or

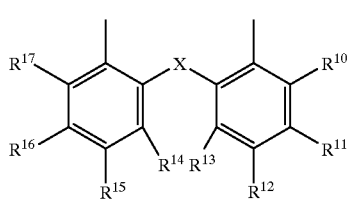

II where:

X is O, S, or $CH(R^{18})$;

$R^{10}$ and $R^{17}$ are the same and are selected from H, $C_1$ to $C_{12}$ alkyl, and $C_1$ to $C_{12}$ alkoxy;

$R^{11}$ and $R^{16}$ are the same and are selected from H, $C_1$ to $C_{12}$ alkyl, and $C_1$ to $C_{12}$ alkoxy;

$R^{12}$ and $R^{15}$ are the same and are selected from H, $C_1$ to $C_{12}$ alkyl, and $C_1$ to $C_{12}$ alkoxy;

$R^{13}$ and $R^{14}$ are the same and are selected from H, $C_1$ to $C_{12}$ alkyl, and $C_1$ to $C_{12}$ alkoxy; and $R^{18}$ is H or $C_1$ to $C_{12}$ alkyl; or

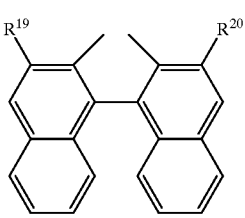

III where:

$R^{19}$ and $R^{20}$ are the same and are selected from H, $C_1$ to $C_{12}$ alkyl, $C_1$ to $C_{12}$ alkoxy, and $CO_2R^{21}$;

$R^{21}$ is $C_1$ to $C_{12}$ alkyl; or phenyl, unsubstituted or substituted with $C_1$ to $C_6$ alkyl; or

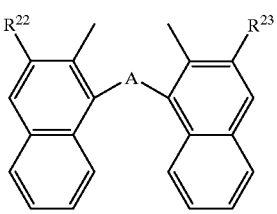

IV where:

A is O, S, $CH(R^{24})$;

$R^{22}$ and $R^{23}$ are the same and are selected from H, $C_1$ to $C_{12}$ alkyl, $C_1$ to $C_{12}$ alkoxy, and $CO_2R^{25}$;

$R^{24}$ is H or $C_1$ to $C_{12}$ alkyl;

$R^{25}$ is $C_1$ to $C_{12}$ alkyl; or phenyl, unsubstituted or substituted with $C_1$ to $C_6$ alkyl;

Examples of organodiphosphites (Ligands) which can be made by this process include those having the formulae V–XI. These organodiphosphites are useful as hydrocyanation catalyst ligands.

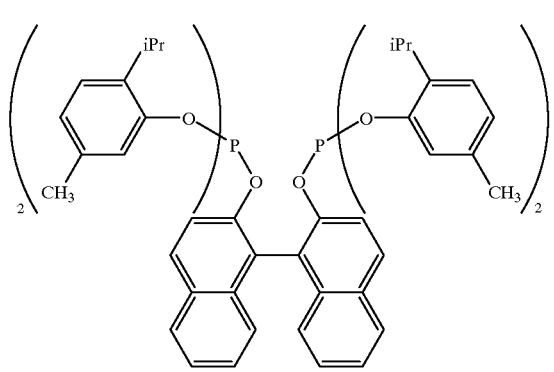
V
(where iPr is isopropyl)
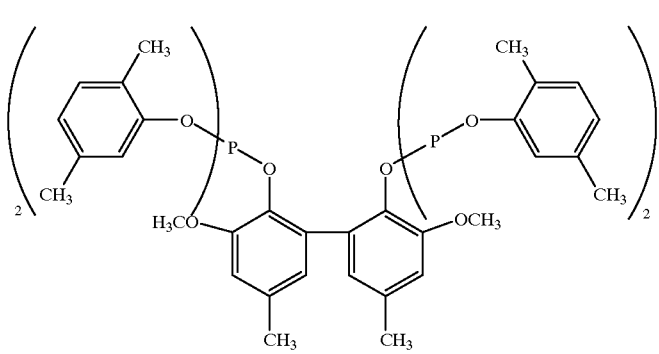
VI
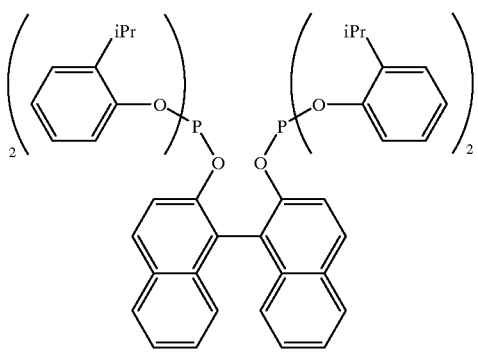
VII
(where iPr is isopropyl)
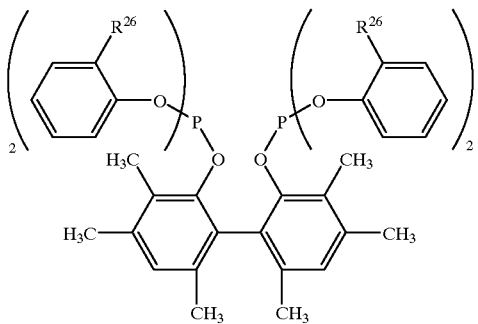
VIII
(where $R^{26}$ is methyl or ethyl)

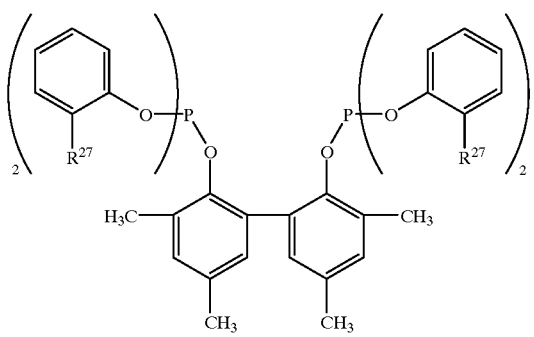

IX (where R²⁷ is methyl, ethyl, or isopropyl)

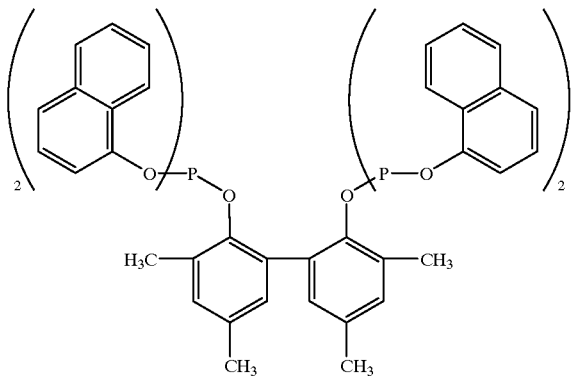

X

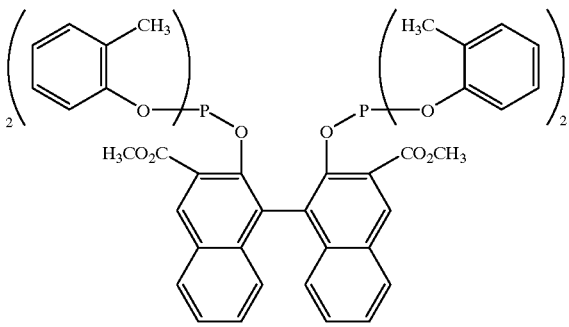

XI

The order of addition of reagents is important to obtaining high selectivity. Adding reagents in an order other than that described will result in lower selectivity to the desired product.

The control of temperature, especially during the first part of the reaction in which the intermediate $(R^1O)_2PCl$ is generated, is critical to the success of this process. Acceptable selectivities may be obtained at temperatures as high as 10° C. However, higher selectivities are obtained at lower temperatures, though little improvement in selectivity is observed below −25° C. Practical considerations, such as the temperature of the available heat exchange medium, such as brine solution, usually dictates the lower practical temperature at which the process may be operated. Because of these considerations, the most preferred operating temperature is in the range of about −10° C. to about 0° C.

The base used in the process of this invention should be anhydrous and soluble in the reaction medium, but the salt of which, generated as a byproduct of its reaction with HCl, should be substantially insoluble. The insolubility of the salt of the base is important for preventing dissociation of the salt to produce small amounts of acid which may catalyze the rearrangement of intermediates and products. It is for this reason that excess base should be utilized. Suitable bases for this process are organic amines. Especially preferred are trialkylamines. The most preferred bases are selected from the group consisting of tributylamine, benzyldimethylamine, triethylamine, and diisopropylmethylamine. It is important to maintain temperature in the −25° C. to 10° C. range during the base addition. The rate of addition of base may be adjusted to maintain temperature in the desired range. It is important that at least two equivalents (per equivalent of $PCl_3$) of base be added in step (b) of the present process to neutralize all of the HCl which is produced from step (a). It is preferred to add at least three equivalents of base in step (b) in order to have sufficient unreacted base in step (c) to neutralize any HCl produced in step (c). Alternatively, less than three equivalents of base may be added in step (b), provided an additional quantity of base is added in step (c) to bring the total number of equivalents of base in the process as a whole to at least three. Because the addition of base results in the formation of an insoluble salt formed by neutralizing HCl, the reaction mixture can become a thick slurry. Such a slurry can create problems in achieving good mixing of base which is important in avoiding temperature gradients in the reaction mixture which can decrease yield of the desired product. It is important, therefore, that the reaction be conducted with vigorous stirring or other agitation to allow effective removal of heat from the reaction mixture. Cooling to the required temperature range can be accomplished by well-known techniques in the art.

The solvents of this process are selected on the basis of their nonreactivity with any reagents or products, their ability to solubilize both reagents and products, their ability to render byproduct salts of the base substantially insoluble, and their having a freezing point below the desired reaction temperature. Additionally, the solvent should be nonreactive with HCl that is generated during the process. Solvents meeting these criteria include both aliphatic and aromatic hydrocarbons and aliphatic nitrile compounds. Preferred solvents are selected from the group consisting of ethers, hexanes, heptanes, octanes, cyclohexane, methylcyclohexane, benzene, toluene, xylenes, acetonitrile, propionitrile, valeronitrile, pentanenitrile and mixtures thereof.

It is important to carry out the present process in the absence of water. It is preferred, therefore, that reagents be dried prior to use and that the reaction itself be carried out under anhydrous conditions. It is also preferred to carry out the present process in the absence of oxygen. Conveniently, the present process may be carried out under a dry, inert atmosphere, such as nitrogen.

The invention is illustrated by the following non-limiting examples.

EXAMPLES

Example 1

Synthesis of Ligand V

This example shows that Ligand V can be produced in high yields by the present process.

A 2-liter, baffled resin kettle was charged with thymol (66.0 g; 439.8 mmol) and toluene (670 mL), and the mixture was cooled to −10° C. The $PCl_3$ (30.0 g, 218.4 mmol) in toluene (30 mL) solution was added, and the temperature was reestablished to −10° C. Then $Et_3N$, triethylamine, (72.0 g; 713 mmol) in toluene (150 mL) solution was added from a dropping funnel over a 30 minute period while stirring at −10° C. for 15 minutes more. Then, 2,2'-binaphthol (31.2 g; 109.2 mmol) in toluene (150 mL) slurry was added over a 30 minute period while maintaining temperature at about 31 10° C. The mixture was warmed to −5° C. and stirred for 1.25 hr. The mixture was then treated with 0.1 N HCl (300 mL) with good mixing and then transferred to a 2 liter separatory funnel. After separating the aqueous layer, the organic layer was treated with 0.1 N NaOH (200 mL), and then distilled water (200 mL). The solvent was removed from the product-containing organic layer under reduced pressure to recover a viscous oil (123 g; analysis by liquid chromatography shows the oil is 71.1% of the compound of Ligand V or 87.5 g of the compound of Ligand V). The yield was 85% based on active ingredients.

Examples 2–5

Effect of Temperature on the Synthesis of Ligand V

These examples show how temperature affects the yield of Ligand V. They also reveal that water, rather than acids and bases, may be used to extract from the product slurry ammonium salts produced from the reaction of the organic base and HCl.

Examples 2–5 were carried out in manner similar to Example 1, except that the acid, base and water extractions were replaced by three water washes (250 mL each). The reaction temperature and the resulting ligand yield were different for each example, as indicated in the table of results below:

| Example | Temperature (C.) | Ligand V Yield (%) |
|---------|------------------|--------------------|
| 2       | −15              | 83                 |
| 3       | −5               | 71                 |
| 4       | 0                | 70                 |
| 5       | 20               | 58                 |

Example 6

Synthesis of Ligand VI

This example shows that Ligand VI can be produced in high yield by the present process.

A 2-liter baffled resin kettle was charged with ortho-cresol (47.5 g; 0.44 mol) and dry toluene (550 mL) and the mixture cooled to −15° C. with a dry ice/acetone bath. $PCl_3$ (30.14 g; 0.22 mol) in toluene (30 mL) was added and the temperature reestablished at −15° C. $Et_3N$ (72.0 g; 0.71 mol) in toluene (150 mL) solution was added dropwise from a dropping funnel over a 2 hr period while maintaining the temperature at about −15° C. and continuing the stirring for an additional 30 minutes. 3,3'-Dimethoxy-5,5'-dimethyl-2,2'-biphenol (30.2 g; 0.11 mol) in toluene (300 mL) was then added dropwise from a dropping funnel over a 1 hr period while maintaining a temperature of −15° C. The reaction mixture was allowed to warm to 0° C. over a 1 hr period and then was extracted with water (3×500 mL). The solvent was removed from the organic layer under reduced pressure to recover a viscous oil. $^{31}P$ nmr analysis reveals about 90selectivity to Ligand VI.

Example 7

Synthesis of Ligand VII

This example shows that Ligand VII can be produced in high yield by the current process.

A 2-liter baffled resin kettle was charged with 2-isopropylphenol (60.0 g; 0.44 mol) and toluene (670 mL) and cooled to about −15° C. $PCl_3$ (30.0 g; 0.22 mol) in toluene (30 mL) was added and the temperature reestablished at −15° C. $Et_3N$ (72.0 g; 0.71 mol) in toluene (150 mL) was added dropwise from a dropping funnel over a 30 minute period while maintaining the reaction mixture at about −8° C. The mixture was stirred for an additional 15 minutes and then a slurry of 2,2'-binaphthol (31.2 g; 0.11 mol) in toluene (150 mL) was added over a 30 minute period while maintaining the temperature at about −8° C. After addition was complete, the reaction mixture was stirred for an additional hour at about −3° C. and then extracted twice with water (2×200 mL). The solvent was removed from the organic layer under reduced pressure to give a viscous oil. $^{31}P$ nmr analysis of the oil showed about 70% selectivity to Ligand VII.

Comparative Example

Synthesis of Ligand V Under the Conditions Described in U.S. Pat. No. 5,235,113

This comparative example shows that when Ligand V is synthesized under the conditions described in U.S. Pat. No. 5,235,113 only low yields of the ligand were obtained.

A 500 mL three-neck round bottom flask equipped with an overhead stirrer, a constant dropping funnel, and an internal thermocouple was charged with toluene (50 mL) and phosphorus trichloride ($PCl_3$; 4.11 g; 0.03 mol). The dropping funnel was charged with a mixture of thymol (9.01 g; 0.060 mol) and triethylamine (6.06 g; 0.060 mol) in toluene (50 mL); this mixture was added to the roundbottom flask dropwise over a 30 minute period at ambient temperature while stirring vigorously and allowed to continue stirring for 1 hour more. A mixture (slurry) comprised of 2,2'-binaphthol (4.29 g; 0.015 mol), triethylamine (3.04 g; 0.030 mol) and toluene (50 mL) was added slowly by pipette over a 30 minute period at ambient temperature while stirring vigorously. After addition was complete, $^{31}P$ nmr analysis revealed that reaction was complete and that a Ligand V yield of less than 10% had been obtained, the remainder of the product being comprised predominantly of monodentate phosphite byproducts.

In a similar reaction in which the temperature was held at 0° C. throughout the reaction, only a 23% yield of Ligand V was observed. In contrast, when Ligand V was synthesized using the process of the present invention, as shown in Example 1, a yield of 85% was obtained.

What is claimed is:

1. A process for the preparation of organodiphosphites of the general formula $(R^1O)_2P(OZO)P(OR^1)_2$ wherein $R^1$ and Z are different substituted or unsubstituted aryl groups, which comprises:
   (a) treating at a temperature between about −25° C. and 10° C. one molar equivalent of $PCl_3$ with about two molar equivalents of $R^1OH$ in the absence of an organic base;
   (b) treating the solution of step (a) at between about −25° C. and 10° C. with at least two equivalents of an organic base to produce $(R^1O)_2PCl$ and a substantially insoluble salt formed from the organic base and HCl which is formed by the reaction of $R^1OH$ and $PCl_3$; and
   (c) reacting at a temperature of between about −25° C. and 10° C. the $(R^1O)_2PCl$ with about one half molar equivalent of HO—Z—OH, provided if less than three equivalents of the organic base are utilized in step (b), then a sufficient quantity of additional organic base is added to bring the total equivalents of organic base utilized in the process to at least three.

2. The process of claim 1 wherein the organodiphosphite is of the formula $(R^1O)_2P(OZO)P(OR^1)_2$ wherein:
   $R^1$ is phenyl, unsubstituted or substituted with one or more $C_1$ to $C_{12}$ alkyl or $C_1$ to $C_{12}$ alkoxy groups; naphthyl, unsubstituted or substituted with one or more $C_1$ to $C_{12}$ alkyl or $C_1$ to $C_{12}$ alkoxy groups; anthracenyl, unsubstituted or substituted with one or more $C_1$ to $C_{12}$ alkyl or $C_1$ to $C_{12}$ alkoxy groups; or phenanthrenyl, unsubstituted or substituted with one or more $C_1$ to $C_{12}$ alkyl or C1 to C12 alkoxy groups;
   Z is selected from radicals defined by the formulae I to IV:

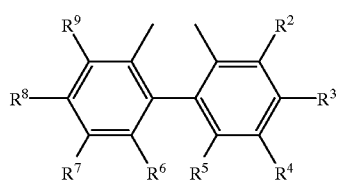

I wherein:

$R^2$ and $R^9$ are the same and are selected from H, $C_1$ to $C_{12}$ alkyl, and $C_1$ to $C_{12}$ alkoxy;
$R^3$ and $R^8$ are the same and are selected from H, $C_1$ to $C_{12}$ alkyl, and $C_1$ to $C_{12}$ alkoxy;
$R^4$ and $R^7$ are the same and are selected from H, $C_1$ to $C_{12}$ alkyl, and $C_1$ to $C_{12}$ alkoxy;
$R^5$ and $R^6$ are the same and are selected from H, $C_1$ to $C_{12}$ alkyl, and $C_1$ to $C_{12}$ alkoxy; or

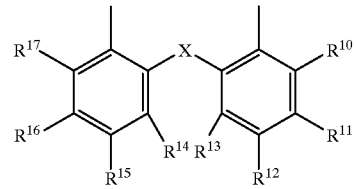

II wherein:
X is O, S, or $CH(R^{18})$;
$R^{10}$ and $R^{17}$ are the same and are selected from H, $C_1$ to $C_{12}$ alkyl, and $C_1$ to $C_{12}$ alkoxy;
$R^{11}$ and $R^{16}$ are the same and are selected from H, $C_1$ to $C_{12}$ alkyl, and $C_1$ to $C_{12}$ alkoxy;
$R^{12}$ and $R^{15}$ are the same and are selected from H, $C_1$ to $C_{12}$ alkyl, and $C_1$ to $C_{12}$ alkoxy;
$R^{13}$ and $R^{14}$ are the same and are selected from H, $C_1$ to $C_{12}$ alkyl, and $C_1$ to $C_{12}$ alkoxy; and
$R^{18}$ is H or $C_1$ to $C_{12}$ alkyl; or

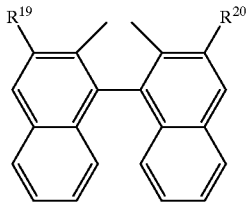

III wherein:
$R^{19}$ and $R^{20}$ are the same and are selected from H, $C_1$ to $C_{12}$ alkyl, $C_1$ to $C_{12}$ alkoxy, and $CO_2R^{21}$,
$R^{21}$ is $C_1$ to $C_{12}$ alkyl; or phenyl, unsubstituted or substituted with $C_1$ to $C_6$ alkyl; or

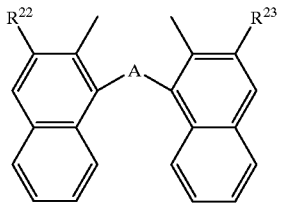

IV wherein:
A is O, S, $CH(R^{24})$;
$R^{22}$ and $R^{23}$ are the same and are selected from H, $C_1$ to $C_{12}$ alkyl, $C_1$ to $C_{12}$ alkoxy, and $CO_2R^{25}$;
$R^{24}$ is H or $C_1$ to $C_{12}$ alkyl;
$R^{25}$ is $C_1$ to $C_{12}$ alkyl; or phenyl, unsubstituted or substituted with $C_1$ to $C_6$ alkyl.

3. The process of claim 1 wherein step (a) is performed at a temperature of between −10° C. and about 0° C.

4. The process of claim 3 wherein steps (b) and (c) are performed at a temperature of between −10° C. and about 0° C.

5. The process of claim 3 wherein Z is a radical of the formula

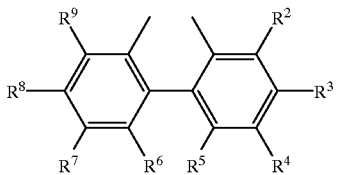

I wherein:

$R^2$ and $R^9$ are the same and are selected from H, $C_1$ to $C_{12}$ alkyl, and $C_1$ to $C_{12}$ alkoxy;

$R^3$ and $R^8$ are the same and are selected from H, $C_1$ to $C_{12}$ alkyl, and $C_1$ to $C_{12}$ alkoxy;

$R^4$ and $R^7$ are the same and are selected from H, $C_1$ to $C_{12}$ alkyl, and $C_1$ to $C_{12}$ alkoxy;

$R^5$ and $R^6$ are the same and are selected from H, $C_1$ to $C_{12}$ alkyl, and $C_1$ to $C_{12}$ alkoxy; or a radical of the formula

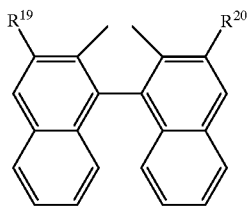

III wherein:

$R^{19}$ and $R^{20}$ are the same and are selected from H, $C_1$ to $C_{12}$ alkyl, $C_1$ to $C_{12}$ alkoxy, and $CO_2R^{21}$; and $R^{21}$ is $C_1$ to $C_{12}$ alkyl; or phenyl, unsubstituted or substituted with $C_1$ to $C_6$ alkyl.

6. The process of claim 3 wherein Z is a radical of the formula

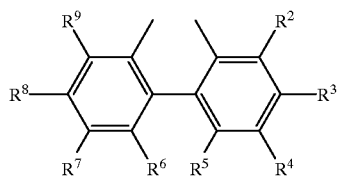

I wherein:

$R^2$ and $R^9$ are the same and are selected from H, $C_1$ to $C_{12}$ alkyl, and $C_1$ to $C_{12}$ alkoxy;

$R^3$ and $R^8$ are the same and are selected from H, $C_1$ to $C_{12}$ alkyl, and $C_1$ to $C_{12}$ alkoxy;

$R^4$ and $R^7$ are the same and are selected from H, $C_1$ to $C_{12}$ alkyl, and $C_1$ to $C_{12}$ alkoxy;

$R^5$ and $R^6$ are the same and are selected from H, $C_1$ to $C_{12}$ alkyl, and $C_1$ to $C_{12}$ alkoxy.

7. The process of claim 3 wherein Z is a radical of the formula

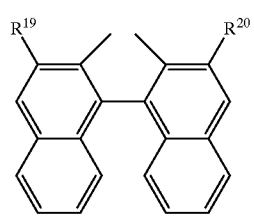

III wherein:

$R^{19}$ and $R^{20}$ are the same and are selected from H, $C_1$ to $C_{12}$ alkyl, $C_1$ to $C_{12}$ alkoxy, and $CO_2R^{21}$; and $R^{21}$ is $C_1$ to $C_{12}$ alkyl; or phenyl, unsubstituted or substituted with $C_1$ to $C_6$ alkyl.

8. The process of claim 5 wherein $R^1$ is selected from the group consisting of phenyl, substituted with one or more $C_1$ to $C_{12}$ alkyl or $C_1$ to $C_{12}$ alkoxy groups; naphthyl, unsubstituted or substituted with one or more $C_1$ to $C_{12}$ alkyl or $C_1$ to $C_{12}$ alkoxy groups; anthracenyl, unsubstituted or substituted with one or more $C_1$ to $C_{12}$ alkyl or $C_1$ to $C_{12}$ alkoxy groups; or phenanthrenyl, unsubstitued or substituted with one or more $C_1$ to $C_{12}$ alkyl or $C_1$ to $C_{12}$ alkoxy groups.

9. The process of claim 8 wherein $R^1$ is selected from the group consisting of 2-methoxyphenyl, 3,5-di-tert-butylphenyl, 9-phenanthrenyl, 2-isopropylphenyl, 2-isopropyl-5-methylphenyl, 2-methylphenyl, 2-ethylphenyl, 2-isopropylphenyl, and 1-naphthyl.

10. The process of claim 9 wherein $R^1$ is selected from the group consisting of 2-isopropylphenyl, 2-isopropyl-5-methylphenyl, 2-methylphenyl, and 2-ethylphenyl.

* * * * *